(12) United States Patent
Sebillotte-Arnaud et al.

(10) Patent No.: US 6,821,942 B2
(45) Date of Patent: Nov. 23, 2004

(54) COSMETIC CLEANSING COMPOSITION

(75) Inventors: Laurence Sebillotte-Arnaud, L'Hay les Roses (FR); Veronique Guillou, Antony (FR)

(73) Assignee: L'Oreal, Paris (FR)

( * ) Notice: Subject to any disclaimer, the term of this patent is extended or adjusted under 35 U.S.C. 154(b) by 52 days.

(21) Appl. No.: 09/903,769

(22) Filed: Jul. 13, 2001

(65) Prior Publication Data

US 2002/0039976 A1 Apr. 4, 2002

(30) Foreign Application Priority Data

Jul. 13, 2000 (FR) .......................................... 00 09226

(51) Int. Cl.$^7$ .............................. C11D 1/72; C11D 3/08; A61K 7/02
(52) U.S. Cl. ..................... 510/466; 510/130; 510/136; 510/152; 510/155; 510/156; 510/421; 510/426; 510/475; 510/505; 510/506; 424/70.1; 424/401
(58) Field of Search ................................ 510/130, 136, 510/152, 155, 156, 421, 426, 466, 475, 505, 506; 424/70.1, 401

(56) References Cited

U.S. PATENT DOCUMENTS

| | | | | |
|---|---|---|---|---|
| 4,450,090 A | | 5/1984 | Kinney ........................ | 252/106 |
| 5,824,296 A | * | 10/1998 | Dubief et al. ............. | 424/70.11 |
| 6,277,797 B1 | * | 8/2001 | Glenn, Jr. et al. .......... | 510/130 |
| 2002/0039976 A1 | * | 4/2002 | Sebillotte-Arnaud et al. .... | 510/119 |

FOREIGN PATENT DOCUMENTS

| | | | | |
|---|---|---|---|---|
| EP | 0 514 760 A1 | | 11/1992 | |
| EP | 514760 | * | 11/1992 | ............ A61K/7/48 |
| EP | 0 692 248 A1 | | 1/1996 | |
| EP | WO 96/28140 | * | 9/1996 | ............ A61K/7/50 |
| EP | 1172095 | * | 1/2002 | ............ A61K/7/48 |
| WO | WO 93/08793 | | 5/1993 | |
| WO | WO 96/28140 | | 9/1996 | |
| WO | WO 97/49381 | | 12/1997 | |
| WO | WO 99/25313 | | 5/1999 | |
| WO | WO 99/38488 | | 8/1999 | |
| WO | WO 00/38621 | | 7/2000 | |

OTHER PUBLICATIONS

T. Someya, et al. Database Caplus, XP–002168470, AN 1987:38232, JP 61180712, "Stable Cleansing Creams." Aug. 13, 1986.

Database WPI, Week 199222, XP–002168471, AN 1992–180847, JP 04120015, Derwent Pulications Ltd., London, GB, Apr. 21, 1992.

Chemical Abstracts, AN 1987:38232, JP 61 180712, Aug. 13, 1986, XP–002168472.

Chemical Abstracts, AN 1992–180847, JP 04 120015, Apr. 21, 1992, XP–002168473.

* cited by examiner

*Primary Examiner*—Brian P Mruk
(74) *Attorney, Agent, or Firm*—Oblon, Spivak, McClelland, Maier & Neustadt, P.C.

(57) ABSTRACT

A cleansing composition, comprising (1) at least one foaming surfactant, (2) at least one hydrophobic silica and (3) at least one oxyalkylenated compound in a physiologically acceptable aqueous medium comprising at least 35% by weight of water relative to the total weight of the composition.

28 Claims, No Drawings

US 6,821,942 B2

COSMETIC CLEANSING COMPOSITION

BACKGROUND OF THE INVENTION

1. Field of the Invention

The present invention relates to a rinsable, foaming, cleansing composition comprising at least one hydrophobic silica and at least one oxyalkylenated compound, and to the use of the composition, in particular, in cosmetics as cleansing products or make-up removing products for the skin, the eyes, the scalp and/or the hair, and for treating greasy skin and/or for disinfecting the skin and/or the scalp.

2. Description of the Background

Cleansing the skin is very important in the care of the face. It must be as efficient as possible since greasy residues, such as excess sebum, the remnants of cosmetic products used daily and make-up products accumulate in the folds of the skin and can block the pores of the skin and result in the appearance of spots.

One means of cleansing the skin properly is to use foaming cleansing products. The foaming cleansing products that are currently commercially available are in the form of foaming bars, gels or creams, and they may or may not contain soaps (fatty acid salts). Soap-containing foaming products have the advantage of giving a creamy lather; however, certain consumers find fault with these products because they cause tautness of the skin because of their excessive detergency. To have a product which is better tolerated by the skin, a desired objective in cleanser formulation is to reduce the soap content of the composition. However, the resulting products then have insufficient viscosity.

Moreover, soap-free foaming products are generally well tolerated by the skin. However, they are generally in the form of liquid products or relatively fluid gels. In order to thicken soap-free foaming products, it is known practice to add thickeners thereto such as alkyl- or acyl-oxyethylenated compounds, polysaccharides such as cellulose derivatives, guar gums and its derivatives, and acrylic polymers. However, in order to increase the viscosity of soap-free foaming products, thereby obtaining products of thick texture, it is necessary to incorporate a large amount of these thickeners into the products. However, when the percentage of alkyl- or acyl-oxyethylenated compounds, such as oxyethylenated alkylglucose esters of which examples include PEG-120 methylglucose dioleate and ceteareth-60 myristyl glycol which are conventionally used, is increased, a formulation is obtained which does not spread uniformly when applied to the skin because it spreads in blobs, which renders these compositions unacceptable to the user. In addition, it is then difficult for lather to develop. Furthermore, it is not possible to increase the percentage of these thickeners indefinitely, because they exceed their solubility limits in the medium.

In addition, when the percentage of cellulose gum, guar gum or acrylic polymer is increased, a product is obtained which exhibits mediocre initial foaming characteristics and which, because the product results in the formation of film-forming deposits that are often difficult to remove by rinsing, give a sensation of poorly cleansed skin.

Thus, there is still a need for foaming cleansing products which are rinsable and thick, but which nevertheless retain the properties required for foaming products, namely good mixing with water, rapid transformation into a lather, good rinsing and good tolerability, in particular, in the case of soap-containing foaming products.

SUMMARY OF THE INVENTION

Accordingly, one object of the present invention is to provide a foaming cleansing composition which is rinsable and thick, and which retains the properties required for foaming products, which are good mixing with water, rapid transformation into a lather, good rinsing and good tolerability, in particular, in the case of soap-containing foaming products.

Briefly, this object and other objects of the present invention as hereinafter will become more readily apparent can be attained by a cleansing composition, comprising:

(1) at least one foaming surfactant, (2) at least one hydrophobic silica and (3) at least one oxyalkylenated compound in a physiologically acceptable aqueous medium comprising at least 35% by weight of water relative to the total weight of the composition.

DETAILED DESCRIPTION OF THE PREFERRED EMBODIMENTS

It has now been found, surprisingly, that the combination of hydrophobic silica and of oxyalkylenated (oxyethylenated and/or oxypropylenated) compound makes it possible to prepare foaming products which flow under their own weight while at the same time being relatively thick, that is to say having a viscosity similar to that of a milk or a thick foaming gel. These products are creamy and cosmetically useful.

Admittedly, it is known practice to use silica in cleansing or detergent compositions. Thus, for example, U.S. Pat. No. 5,880,076 discloses a liquid detergent composition which may contain silicas. EP 0 550 281 and U.S. Pat. No. 5,389,279 mention silica as a powder which may be incorporated into cleansing compositions. However, the silicas used alone in the known soap-free foaming products do not efficiently thicken the soap product and give the desired rheology, and no document discloses a combination of hydrophobic silica and an oxyalkylenated compound to thicken foaming products.

The expression "physiologically acceptable medium" means herein a medium which is compatible with the skin, mucous membranes, the scalp, the eyes and/or the hair. Moreover, it is an aqueous medium, i.e. a medium comprising an amount of water of at least 35% by weight, preferably ranging from 35% to 95% by weight and better still from 40% to 90% by weight relative to the total weight of the composition.

The compositions of the invention are foaming and rinsable cleansing compositions. They are in the form of a gel which can flow under its own weight without being fluid, that is to say a gel which has a viscosity which may range, for example, from 70 poises to 200 poises (7 to 20 Pa.s) and preferably from 90 poises to 150 poises (9 to 15 Pa.s), the viscosity being measured at 25° C. with a Rheomat 180 measuring machine at 180 to 200 $s^{-1}$, this machine being equipped with a different spindle depending on the viscosities, for example a No. 2 spindle for viscosity ranges of less than 7 poises, a No. 3 spindle for viscosity ranges from 2 to 40 poises and a No. 4 spindle for viscosity ranges of greater than 20 poises.

Hydrophobic Silicas

In the present application the term "hydrophobic silica" means both pure hydrophobic silicas and particles coated with hydrophobic silica.

The amount of hydrophobic silica(s) in the composition of the invention, whether it is pure silica or particles coated with hydrophobic silica, is preferably at least 1% on an active material weight basis relative to the total weight of the composition, and it may range, for example, on an active material weight basis, from 1% to 15% by weight, preferably from 2% to 10% by weight and more preferably from 2% to 6% by weight relative to the total weight of the composition.

The hydrophobic silicas which may be used in the composition of the invention are preferably amorphous and of pyrogenic origin. They exist preferably in pulverulent form.

Amorphous hydrophobic silicas of pyrogenic origin are obtained from hydrophilic silicas. These hydrophilic silicas are obtained by continuous flame pyrolysis at 1000° C. of silicon tetrachloride ($SiCl_4$) in the presence of hydrogen and oxygen. They are then made hydrophobic by a treatment with halosilanes, alkoxysilanes or silazanes. Hydrophobic silicas differ from the hydrophilic starting silicas by, inter alia, a lower density of silanol groups and a smaller adsorption of water vapor.

According to a preferred embodiment of the invention, the hydrophobic silica is selected from silicas having a specific surface ranging from 50 to 500 $m^2/g$, a number-average particle size ranging from 3 to 50 nm and a compacted density ranging from 40 to 200, preferably from 50 to 150 g/l. They are more particularly the hydrophobic silicas described in Table (1) below, and mixtures thereof.

TABLE 1

| | Trade name | | | | |
|---|---|---|---|---|---|
| | Aerosil R202 (from Degussa-Huels) | Aerosil R805 (from Degussa-Huels) | Aerosil R812 (from Degussa-Huels) | Aerosil R972 (from Degussa-Huels) | Aerosil R974 (from Degussa-Huels) |
| BET surface ($m^2/g$) | 90 ± 20 | 150 ± 25 | 260 ± 30 | 110 ± 20 | 170 ± 20 |
| Average particle size (nm) | 14 | 12 | 7 | 16 | 12 |
| Compacted density (g/l) | about 50 | about 50 | about 50 | about 50 | about 50 |
| pH at 4% in water | 4–6 | 3.5–5.5 | 5.5–7.5 | 3.6–4.3 | 3.4–4.2 |

The hydrophobic silica employed in the composition of the invention may also consist of a particle which is totally or partially coated with silica, in particular a mineral particle totally or partially coated with silica, such as the pigments and metal oxides coated with hydrophobic silica. These particles may also have optical properties in the product and on the skin; for example, they may have a matt effect or a slightly whitening effect.

The hydrophobic silicas sold under the names Aerosil R972° by the company Degussa-Huels are preferably used as hydrophobic silica.

Oxyalkylenated Compounds

The oxyalkylenated compound(s) which may be used in the composition of the invention may comprise ethylene oxide groups (oxyethylenated compounds), propylene oxide groups (oxypropylenated compounds) or both (oxyethylenated/oxypropylenated compounds).

One or more oxyalkylenated compounds may be used, and the amount of oxyalkylenated compound in the composition of the invention may range, for example, on an active material weight basis, from 1% to 20% by weight and better still from 2% to 10% by weight relative to the total weight of the composition.

Suitable oxyalkylenated compounds include, in particular, polyethylene glycols, polyethylene glycol esters and/or polypropylene glycol esters, polyethylene glycol ethers and/or polypropylene glycol ethers, alkoxylated aryl derivatives and in particular ethoxylated aryl polyol derivatives, oxyalkylenated and in particular oxyethylenated triesters of glycerol and of fatty acids, ethoxyethylenated urethane derivatives modified with alkyl chains, and mixtures thereof.

1. The polyethylene glycols which may be used in the composition of the invention are ethylene oxide polycondensates having a number of ethylene oxide (EO) units of greater than 10. The ethylene oxide number may range, for example, from 10 to 50 000 and preferably from 14 to 10 000. Suitable examples of polyethylene glycols include polyethylene glycol comprising 7 000 EO (CTFA name: PEG-7M), for instance the product sold under the name Polyox WSR N-750® by the company Amerchol, polyethylene glycol comprising 75 EO (CTFA name: PEG-75), polyethylene glycol comprising 20,000 EO (CTFA name: PEG-20M), for instance the product sold under the name Polyox WSR 1105® by the company Amerchol, and polyethylene glycol comprising 150 EO (CTFA name: PEG-150).

2. The polyethylene glycol esters and/or polypropylene glycol esters are condensates of polyethylene glycol and/or polypropylene glycol with one or more fatty acids. These compounds have the formula:

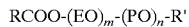

$RCOO\text{-}(EO)_m\text{-}(PO)_n\text{-}R'$ in which $0<m\leq300$ and $0\leq n\ 300$ and $m+n\geq6$, R and R' represent, independently of each other, hydrogen or a saturated or unsaturated, linear or branched, hydroxylated or non-hydroxylated alkyl chain containing from 1 to 30 carbon atoms and preferably from 12 to 22 carbon atoms, or an aryl chain, on condition that R and R' are not simultaneously hydrogen.

Suitable examples of polyethylene glycol acid esters and/or polypropylene glycol acid esters include polyethylene glycol distearate (150 EO), such as the product sold under the name Atlas G-1821® by the company Uniqema, PEG-150 dibehenate, such as the product sold under the name Ethox PEG 6000 Dibehenate® by the company Ethox, polyethylene glycol palmitostearate (120 EO), such as the product sold under the name Stearate 6000 WL 1644® by the company Gattefosse, the copolymer of polyethylene glycol ligand (30 EO) and of 12-hydroxystearic acid, such as the product sold under the name Arlacel P135® by the company Uniqema, and polyethylene glycol stearate (40 EO), such as the product sold under the name MYRJ 52® by the company Uniqema. In the case where R=R'=H, mention may be made, for example, of the polyoxyethylene/polyoxypropylene statistic copolymer (17 EO/6 PO) sold under the name UCON 75-H-450® by the company AMERCHOL. Molecules having more EO and/or more PO are not excluded.

3. The polyethylene glycol ethers and/or polypropylene glycol ethers are condensates of polyethylene glycol and/or polypropylene glycol with one or more fatty alcohols. These are compounds of formula:

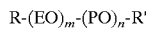

$R\text{-}(EO)_m\text{-}(PO)_n\text{-}R'$ in which $0\leq m\leq300$ and $0\leq n\leq300$ and $m+n\geq6$, R and R' represent, independently of each other, hydrogen or a saturated or unsaturated, linear or branched, hydroxylated or non-hydroxylated alkyl chain containing from 1 to 30 carbon atoms and preferably from 12 to 22 carbon atoms, or an aryl chain, on condition that R and R' are not simultaneously hydrogen.

Suitable examples of polyethylene glycol ethers include, in particular oxyethylenated (30 EO) cetyl alcohol, such as the product sold under the name Nikkol BC-30TX t® by the company Nikkol, oxyethylenated (15 EO) oleyl alcohol, such as the product sold under the name Nikkol BO-15T® by the company Nikkol, oxyethylenated (50 EO) oleyl alcohol, such as the product sold under the name Nikkol BO-50® by the company Nikkol, oxyethylenated (10 EO) behenyl alcohol, such as the product sold under the name Mergital B 10® by the company Nikkol, oxyethylenated (30 EO) behenyl alcohol, such as the product sold under the name Nikkol BB-30® by the company Nikkol, oxyethylenated (12 EO) lauryl alcohol, such as the product sold under the name Rewopal 12® by the company Goldschmidt, oxyethylenated (23 EO) lauryl alcohol, such as the product sold under the name Simulsol P 23® by the company SEPPIC, oxyethylenated (20 EO) 2-octyldodecyl alcohol, such as the product sold under the name Octyldodeceth-20® by the company Stearinerie Dubois, oxyethylenated (20 EO) isocetyl alcohol, such as the product sold under the name Arlasolve 200 US® by the company Uniqema, oxyethylenated (10 EO) oleyl alcohol, such as the product sold under the name Brij 97® by the company Uniqema, oxyethylenated (20 EO) oleyl alcohol, such as the product sold under the name Brij 98® by the company Uniqema, oxyethylenated (100 EO) stearyl alcohol, such as the product sold under the name Brij 700® by the company Uniqema, and oxyethylenated (21 EO) stearyl alcohol, such as the product sold under the name Brij 721® by the company Uniqema.

Suitable examples of polyethylene glycol/polypropylene glycol ethers include, in particular, oxyethylenated (5 EO) oxypropylenated (5 PO) lauryl alcohol, such as the product sold under the name Aethoxal B® by the company Cognis, oxypropylenated (3 PO) myristyl alcohol, such as the product sold under the name Promyristyl PM-3® by the company Croda, oxyethylenated (20 EO) oxypropylenated (5 PO) cetyl alcohol, such as the product sold under the name Procetyl AWS® by the company Croda, oxyethylenated (26 EO) oxypropylenated (26 PO) butyl alcohol, such as the product sold under the name PPG-26-Buteth-26® by the company Goldschmidt, oxyethylenated (26 EO) oxypropylenated (26 PO) butyl alcohol, such as the product sold under the name Varonic Apeb® by the company Goldschmidt, oxyethylenated (30 EO) oxypropylenated (6 PO) decyltetradecanol, such as the product sold under the name Nikkol PEN-4630® by the company Nikkol, and oxyethylenated (25 EO) oxypropylenated (25 PO) lauryl alcohol, such as the product sold under the name ADF-Olcile® by the company Vevy.

4. The ethoxylated alkyl or aryl derivatives of polyol include, for example, oxyethylenated derivatives of fatty acid esters or of fatty alcohol ethers and of a polyol such as glycerol, sorbitol, glucose or pentaerythritol.

Suitable derivatives of this type include, for example, oxyethylenated (78 EO) glyceryl cocoate, such as the product sold under the name Simulsol CG by the company SEPPIC, oxyethylenated (120 EO) methylglucose dioleate, such as the product sold under the name Glucamate DOE-120 Vegetal® by the company Amerchol, oxyethylenated (40 EO) sorbitan septaoleate, such as the product sold under the name Arlatone T® by the company Uniqema, oxyethylenated (10 EO) polyglyceryl (2 mol of glycerol) laurate, such as the product sold under the name HOE S 3495® by the company Clariant, oxyethylenated (60 EO) glyceryl isostearate, such as the product sold under the name Emalex GWIS-160® by the company SACI-CFPA, oxyethylenated (20 EO) glyceryl monostearate, such as the product sold under the name Cutina E 24® by the company Cognis, oxyethylenated (200 EO) glyceryl stearate, such as the product sold under the name Simulsol 220 TM® by the company SEPPIC, and oxyethylenated (150 EO) pentaerythrityl tetrastearate, such as the product sold under the name Crothix® by the company Croda.

5. Oxyalkylenated glyceryl triesters of fatty acids include, for example, oxyethylenated (6 EO) caprylic/capric acid glycerides, such as the product sold under the name Softigen 767® by the company Condea, and oxyethylenated (50 EO) olive oil, such as the product sold under the name Crovol 0-70® by the company Croda.

6. Ethoxyethylenated urethane derivatives modified with alkyl chains include, for example, those of formula (1) and (2):

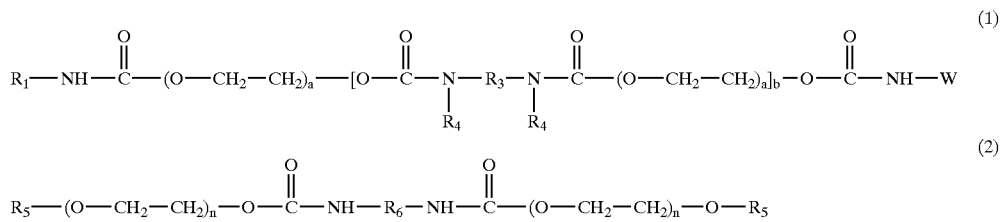

wherein radicals $R_1$, $R_2$ and $R_5$ represent a $C_{1-18}$ alkyl group; $R_3$ and $R_6$ represent a linear, cyclic or aromatic $C_{4-36}$ hydrocarbon-based radical; $R_4$ represents a hydrogen atom or a $C_{1-6}$ alkyl radical, preferably a hydrogen atom; a is an integer ranging from 90 to 600 and b is an integer ranging from 1 to 4.

Examples of these urethane derivatives include, for example, water-soluble polymers prepared by the addition reaction of diisocyanates (HMDI: hexamethylene diisocyanate) with diols (polyether, polyesters) and ending with hydrophobic groups obtained from ethoxylated or ethoxylated/propoxylated fatty alcohols. This is the case, for example, for SER AD FX 1100 sold by the company Adriss, which is an oxyethylenated (100 EO) stearyl alcohol/polyethylene glycol (136 EO)/hexamethylene diisocyanate copolymer.

Polymers of this type include, for example, the products sold under the names Acrysol 44 (or Aculyn 44) and Acrysol 46 (or Aculyn 46) (CTFA name: PEG-150/Decyl alcohol/

SMDI Copolymer), which are polyurethanes obtained by condensation of hexamethylene diisocyanate and of polyethylene glycol, bearing a methyl residue and an octadecyl residue at their termini, respectively. These polyurethanes also contain from 3% to 5% of an enzymatically modified starch matrix. The polyurethanes are sold by Rohm & Haas. The compounds are the products Rheolate® 205, 210, 212, 216, 244, 278, 255, 266, 288, 300 and 350 sold by the company Elementis or the products Borchigel LW.44, L.75.N; L 76; VP 9628-LL36; VP 97105-NT40; VP 9620 sold by the company Borchers.

Surfactants

The foaming composition of the invention contains at least one surfactant which imparts a foaming nature to the composition. This surfactant may be selected from nonionic, anionic, amphoteric and zwitterionic foaming surfactants and mixtures thereof.

The amount of surfactants may range, for example, on an active material weight basis, from 2% to 50% by weight, preferably from 3% to 30% by weight relative to the total weight of the composition.

1. Nonionic surfactants:

Nonionic surfactants which may be used, for example, include alkyl polyglucosides (APGs), maltose esters, polyglycerolated fatty alcohols, glucamine derivatives such as 2-ethylhexyloxycarbonyl-N-methylglucamine, and mixtures thereof.

Alkyl polyglucosides which are preferably used are those containing an alkyl group containing from 6 to 30 carbon atoms and preferably from 8 to 16 carbon atoms, and containing a hydrophobic group (glucoside) preferably comprising from 1.2 to 3 saccharide units. Alkyl polyglucosides include, for example, decylglucoside (AlkylC9/C11-polyglucoside (1.4)), such as the product sold under the name Mydol 10® by the company Kao Chemicals, the product sold under the name Plantaren 2000 UP® by the company Henkel and the product sold under the name Oramix NS 10® by the company SEPPIC; caprylyl/capryl glucoside, such as the product sold under the name Oramix CG 110® by the company SEPPIC; laurylglucoside, such as the products sold under the names Plantaren 1200 N® and Plantacare 1200® by the company Henkel; and cocoglucoside, such as the product sold under the name Plantacare 818/UP® by the company Henkel.

The maltose derivatives include, for example, those disclosed in document EP-A-566 438, such as O-octanoyl-6'-D-maltose or O-dodecanoyl-6'-D-maltose disclosed in document FR-2 739 556.

Suitable polyglycerolated fatty alcohols include polyglycerolated dodecanediol (3.5 mol of glycerol), this product being sold under the name Chimexane NF® by the company Chimex.

2. The anionic surfactants may be selected, in particular, from carboxylates, amino acid derivatives, alkyl sulfates, alkyl ether sulfates, sulfonates, isethionates, taurates, sulfosuccinates, alkyl sulfoacetates, phosphates and alkyl phosphates, polypeptides, anionic alkyl polyglucoside derivatives and fatty acid soaps, and mixtures thereof.

Carboxylates include, for example, alkali metal salts of N-acylamino acids; amido ether carboxylates (AECs), for instance sodium lauryl amido ether carboxylate (3 EO) sold under the name Akypo Foam 30® by the company Kao Chemicals; polyoxyethylenated carboxylic acid salts, for instance oxyethylenated (6 EO) sodium lauryl ether carboxylate (C12-14-16 65/25/10) sold under the name Akypo Soft 45 NV® by the company Kao Chemicals; polyoxyethylenated fatty acids of olive oil and of carboxymethyl, this product being sold under the name Olivem 400® by the company Biologia E Technologia; oxyethylenated (6 EO) sodium tridecyl ether carboxylate sold under the name Nikkol ECTD-6NEX® by the company Nikkol.

The amino acid derivatives may be selected, for example, from sarcosinates and in particular acylsarcosinates, for instance the sodium lauroyl sarcosinate sold under the name Sarkosyl NL 97® by the company Ciba or sold under the name Oramix L 30® by the company SEPPIC, the sodium myristoyl sarcosinate sold under the name Nikkol Sarcosinate MN® by the company Nikkol or the sodium palmitoyl sarcosinate sold under the name Nikkol Sarcosinate PN® by the company Nikkol; alaninates, for instance the sodium N-lauroyl-N-methylamidopropionate sold under the name Sodium Nikkol Alaninate LN 30® by the company Nikkol or sold under the name Alanone ALE® by the company Kawaken, and the N-lauroyl-N-methylalanine triethanolamine sold under the name Alanone Alta® by the company Kawaken; N-acylglutamates, for instance the triethanolamine monococoylglutamate sold under the name Acylglutamate CT-12® by the company Ajinomoto and the triethanolamine lauroylglutamate sold under the name Acylglutamate LT-12® by the company Ajinomoto; aspartates, for instance the mixture of triethanolamine N-lauroyl aspartate and of triethanolamine N-myristoylaspartate, sold under the name Asparack® by the company Mitsubishi; citrates, and mixtures thereof.

Suitable alkyl ether sulfates include, for example, the sodium lauryl ether sulfate (C12–14 70/30) (2.2 EO) sold under the names Sipon AOS 225® or Texapon N702 PATE® by the company Henkel, the ammonium lauryl ether sulfate (C12–14 70/30) (3 EO) sold under the name Sipon Lea 370® by the company Henkel, and the ammonium ($C_{12}$–$C_{14}$) alkyl ether (9 EO) sulfate sold under the name Rhodapex AB/20® by the company Rhodia Chimie.

Suitable sulfonates include, for example, α-olefin sulfonates, for instance the sodium α-olefin sulfonate (C14–16) sold under the name Bio-Terge AS-40® by the company Stepan, sold under the names Witconate AOS Protégé® and Sulframine AOS PH 12® by the company Witco or sold under the name Bio-Terge AS-40 CG® by the company Stepan, the sodium secondary olefin sulfonate sold under the name Hostapur SAS 30® by the company Clariant; linear alkyl aryl sulfonates, for instance the sodium xylenesulfonate sold under the names Manrosol SXS30®, Manrosol SXS40® and Manrosol SXS93® by the company Manro.

Suitable isethionates include acylisethionates, for instance sodium cocoylisethionate, such as the product sold under the name Jordapon CI P® by the company Jordan.

Suitable taurates include the sodium salt of palm kernel oil methyltaurate sold under the name Hostapon CT Pate® by the company Clariant; N-acyl N-methyltaurates, for instance the sodium N-cocoyl N-methyltaurate sold under the name Hostapon LT-SF® by the company Clariant or sold under the name Nikkol CMT-30-T® by the company Nikkol, and the sodium palmitoyl methyltaurate sold under the name Nikkol PMT® by the company Nikkol.

Suitable sulfosuccinates include, for example, the oxyethylenated (3 EO) lauryl monosulfosuccinate (C12/C14 70/30) sold under the names Setacin 103 Special®, Rewopol SB-FA 30 K 4® by the company Witco, the disodium salt of a $C_{12}$–$C_{14}$-alkyl hemisulfosuccinate, sold under the name Setacin F Special Paste® by the company Zschimmer Schwarz, the oxyethylenated (2 EO) disodium oleamidosulfosuccinate sold under the name Standapol HS 135® by the company Henkel, the oxyethylenated (5 EO) laurylamide monosulfosuccinate sold under the name Lebon A-5000® by the company Sanyo, the oxyethylenated (10 EO) disodium salt of lauryl citrate monosulfosuccinate sold under the name Rewopol SB CS 50® by the company Witco, and the ricinoleic monoethanolamide monosulfosuccinate sold under the name Rewoderm S 1333® by the company Witco.

Suitable phosphates and alkyl phosphates include, for example, monoalkyl phosphates and dialkyl phosphates, such as the lauryl monophosphate sold under the name MAP 20® by the company Kao Chemicals, the potassium salt of dodecylphosphoric acid, as a mixture of monoester and diester (mainly diester), sold under the name Crafol AP-31® by the company Cognis, the mixture of monoester and diester of octylphosphoric acid, sold under the name Crafol AP-20® by the company Cognis, the mixture of ethoxylated (7 mol of EO) phosphoric acid monoester and diester of 2-butyloctanol, sold under the name Isofol 12 7 EO-Phosphate Ester® by the company Condea, the potassium salt or triethanolamine salt of monoalkyl ($C_{12}$–$C_{13}$-) phosphate sold under the references Arlatone MAP 230K-40® and Arlatone MAP 230T-60® by the company Uniqema, and the potassium lauryl phosphate sold under the name Dermalcare MAP XC-99/09® by the company Rhodia Chimie.

The polypeptides are obtained, for example, by coupling a fatty chain with amino acids from cereals and in particular from wheat and oat. Suitable polypeptides include, for example, the potassium salt of hydrolysed lauroyl wheat protein, sold under the name Aminofoam W OR® by the company Croda, the triethanolamine salt of hydrolysed cocoyl soybean protein, sold under the name May-Tein SY® by the company Maybrook, the sodium salt of oat lauroylamino acids, sold under the name Proteol Oat® by the company SEPPIC, the collagen hydrolysate grafted onto coconut fatty acid, sold under the name Geliderm 3000® by the company Deutsche Gelatine, and the soybean proteins acylated with hydrogenated coconut acids, sold under the name Proteol VS 22® by the company SEPPIC.

Suitable anionic derivatives of alkylpolyglucosides include, in particular, glyceryl ethers, carbonates, sulfosuccinates, tartrates and citrates obtained from alkyl polyglucosides. Suitable examples include the sodium salt of cocoylpolyglucoside (1,4) tartaric ester, sold under the name Eucarol AGE-ET® by the company Cesalpinia, the disodium salt of cocoylpolyglucoside (1,4) sulfosuccinic ester, sold under the name Essai 512 MP® by the company SEPPIC, and the sodium salt of cocoylpolyglucoside (1,4) citric ester, sold under the name Eucarol AGE-EC® by the company Cesalpinia.

The fatty acid soaps employed as anionic surfactants include fatty acids of natural or synthetic origin, salified with a mineral or organic base. The fatty chain may comprise from 6 to 22 carbon atoms and preferably from 8 to 18 carbon atoms. The mineral or organic base may be selected from alkali metals or alkaline earth metals, amino acids and amino alcohols. Suitable salts include, for example, the sodium, potassium, magnesium, triethanolamine and N-methylglucamine salts of lysine and of arginine. Suitable soaps include, for example, the potassium and sodium salts of lauric, myristic, palmitic or stearic acid (potassium or sodium laurate, myristate, palmitate and stearate), and mixtures thereof.

3. The amphoteric and zwitterionic surfactants may be selected, for example, from betaines, N-alkylamidobetaines and derivatives thereof, glycine derivatives, sultaines, alkyl polyaminocarboxylates and alkylamphoacetates, and mixtures thereof.

Suitable betaines include cocobetaine, for instance, the product sold under the name Dehyton AB-30® by the company Henkel, laurylbetaine, for instance the product sold under the name Genagen KB® by the company Clariant, oxyethylenated (10 EO) laurylbetaine, for instance the product sold under the name Lauryl Ether (10 EO) Betaine® by the company Shin Nihon Rica, and oxyethylenated (10 EO) stearylbetaine, for instance the product sold under the name Stearyl Ether (10 EO) Betaine® by the company Shin Nihon Rica.

Suitable among the N-alkylamidobetaines and derivatives thereof include, for example, the cocamidopropylbetaine sold under the name Lebon 2000 HG® by the company Sanyo, or sold under the name Empigen BB® by the company Albright & Wilson, and the lauramidopropyl betaine sold under the name Rewoteric AMB 12P® by the company Witco. Suitable glycine derivatives include the sodium N-cocoylglycinate sold under the name Amilite GCS-12® by the company Ajinomoto.

Sultaines which may be mentioned include the cocoylamidopropylhydroxysulfobetaine sold under the name Crosultaine C-50 by the company Croda.

Suitable alkyl polyaminocarboxylates (APACs) include the sodium cocoylpolyaminocarboxylate sold under the name Ampholak 7 CX/C® and Ampholak 7 CX® by the company Akzo Nobel, the sodium stearylpolyamidocarboxylate sold under the name Ampholak 7 TX/C by the company Akzo Nobel and the sodium carboxymethyloleylpolypropylamine sold under the name Ampholak X07/C® by the company Akzo Nobel.

Suitable alkylamphoacetates include, for example, N-disodium N-cocoyl-N-carboxymethoxyethyl-N-carboxymethylethylenediamine (CTFA name: disodium cocamphodiacetate), for instance the product sold under the name Miranol C2M Concentré NP® by the company Rhodia Chimie and N-sodium N-cocoyl-N-hydroxyethyl-N-carboxymethylethylenediamine (CTFA name: sodium cocamphoacetate).

According to one particular embodiment of the invention, of the surfactants mentioned above, the anionic surfactants more particularly used are acylsarcosinates, oxyethylenated alkyl ether sulfates, N-aryl N-methyltaurates, N-acylglutamates, acylisethionates, sulfosuccinates, phosphates and alkyl phosphates, polypeptides and soaps; the amphoteric and zwitterionic surfactants more particularly used are betaines and alkylamphoacetates; the nonionic surfactants more particularly used are alkyl polyglucosides, O-octanoyl-6'-D-maltose, O-dodecanoyl-6'-D-maltose, polyglycerolated dodecanediol (3.5 mol of glycerol) and 2-ethylhexyloxycarbonyl-N-methylglucamine; and mixtures of these surfactants.

The aqueous medium of the composition of the invention may contain, in addition to water, one or more solvents selected from lower alcohols containing from 1 to 6 carbon atoms, such as ethanol; and polyols. Suitable polyols include glycerol; glycols, for instance butylene glycol, isoprene glycol, propylene glycol and polyethylene glycols such as PEG-8; sorbitol; sugars such as glucose, fructose, maltose, lactose or sucrose; and mixtures thereof. The amount of solvent in the composition of the invention may range, for example, from 0.5% to 30% by weight and preferably from 2% to 20% by weight relative to the total weight of the composition.

The compositions of the invention may contain adjuvants usually used in cosmetics, and in particular those used in cleansing products. Suitable adjuvants, for example, include fragrances, preserving agents, sequestering agents (EDTA), pigments, nacres, mineral or organic fillers, matt-effect agents, bleaching or exfoliant agents, soluble colorants, sun-screens, cosmetic or dermatological active agents such as water-soluble or liposoluble vitamins, antiseptics, antiseborrhoeic agents, antimicrobial agents such as benzoyl peroxide, salicylic acid, triclosan and azelaic acid, and also optical brighteners, nonionic polymers such as polyvinylpyrrolidone (PVP), anionic and amphoteric polymers, and fatty substances that are incompatible with the aqueous medium, for instance oils or waxes. The amounts of these various adjuvants are those conventionally used in the field under consideration, and, range, for example, from 0.01% to 20% of the total weight of the composition. These adjuvants and their concentrations must be such that they do not modify the desired property for the composition of the invention.

Suitable fillers include, for example, mineral fillers such as talc or magnesium silicate (size: 5 microns) sold under the name LUZENAC 15 M00® by the company LUZENAC; kaolin or aluminum silicate such as, for example, the product sold under the name KAOLIN SUPREME by the company IMERYS; and organic fillers such as starch such as, for example, the product sold under the name AMIDON DE MAIS B by the company ROQUETTE, nylon microspheres such as those sold under the name Orgasol 2002 UD NAT COS by the company Atochem; microspheres based on vinylidene chloride/acrylonitrile/methacrylonitrile copolymer, containing isobutane, expanded such as those sold under the name Expancel 551 DE by the company EXPANCEL. It is possible also to add in the composition of the invention, fibers such as, for example, the nylon fibers (Polyamide 0.9 Dtex 0.3 mm, sold by Etablissements Paul Bonte), cellulose or rayon fibers (RAYON FLOCK RCISE N0003 M04® sold by the company CLAREMONT FLOCK CORPORATION).

The compositions of the invention may in particular constitute cleansing or make-up-removing products for the skin (body, face and eyes), the scalp and/or the hair.

Another aspect of the invention is the cosmetic use of the composition as defined above, as a product for cleansing and/or for removing make-up from the skin, the eyes, the scalp and/or the hair.

The compositions of the invention may also constitute compositions for treating greasy skin and/or for disinfecting the skin and/or the scalp, in particular when they contain an antibacterial agent. In particular, specific active agents for treating greasy skin may be included therein, such as, for example, salicylic acid, azelaic acid, triclosan, piroctone olamine or niacinamide (vitamin PP).

Still another aspect of the invention is the use of the composition as defined above for the preparation of a composition intended for treating greasy skin and/or for disinfecting the skin and/or the scalp.

Yet another subject of the invention is a process for cleansing the skin, the eyes, the scalp and/or the hair, wherein the composition of the invention is applied to the skin, the eyes, the scalp and/or the hair, in the presence of water, and the lather formed and the soiling residues are removed by rinsing with water.

In the case of cleansing the face, the composition of the invention may constitute a mask which is removed by rinsing after it has been left on the skin for a period of 1 to 3 minutes.

Having now generally described this invention, a further understanding can be obtained by reference to certain specific examples which are provided herein for purposes of illustration only and are not intended to be limiting unless otherwise specified. The amounts indicated are percentages by weight, except where otherwise mentioned.

EXAMPLE 1 AND COMPARATIVE EXAMPLES 1 AND 2

Soap-free Compositions

| Compositions | Comparative Ex.1 | Comparative Ex.2 | Ex. 1 Of the invention |
|---|---|---|---|
| Cocabetaine [Dehyton AB-30°® at 30% active material (A.M.)] | 9.75% (in A.M.) | 9.75% (in A.M.) | 9.75% (in A.M.) |
| Sodium laureth sulphate (2.2 EO) [Texapon N702 Pâte ® at 70% active material (A.M.)] | 2.6% (in A.M.) | 2.6% (in A.M.) | 2.6% (in A.M.) |
| PEG-120 methyl glucose dioleate (Glucamate DOE-120 Vegetal ®) | 4% | 0 | 4% |
| Hydrophobic silica (Aerosil R-972 ®) | 0 | 5% | 5% |
| Sorbitol | 3.5% | 3.5% | 3.5% |
| Glycerol | 3.5% | 3.5% | 3.5% |
| Preserving agents | qs | qs | qs |
| Water | qs 100 g | qs 100 g | qs 100 g |
| Appearance | Fluid runny crystalline gel | Liquid product | Thick translucent gel |
| pH | 7 | 6.7 | 6.6 |
| Viscosity using a Rheomat 180, spindle No. 4 at about 25° C. | 59 poises (= 5.9 Pa · s) | 1 to 100 cpoises (1 to 100 mPa · s) | 97 poises (9.7 Pa · s) |

The composition of the invention has the advantage of being in the form of a thick gel, which is easier to use than a runny gel, and of having good cosmetic properties.

EXAMPLE 2

Soap-free Foaming Composition

| | |
|---|---|
| Lauryl monophosphate (containing 75% monoester) (MAP 20 ®) | 6.5% (in A.M.) |
| Alkyl-C9/C11-polyglucoside (1.4) (Mydol 10) | 6.5% (in A.M.) |
| Potassium hydroxide | 1.7% |
| PEG-120 methylglucose dioleate (Glucamate DOE-120 Vegetal ®) | 2% |
| Hydrophobic silica (Aerosil R-972 ®) | 5% |
| Preserving agents | qs |
| Water | qs 100% |

The composition is in the form of a thick runny gel with a pH of 7.1, having a viscosity of 142 poises (14.2 Pa.s) measured at 25° C. with a Rheomat 180 viscometer fitted with a No. 4 spindle.

Sensory Performance Qualities:

The developed foam qualities are evaluated according to the protocol described below.

Before any use of the products, the hands are washed with household soap and then suitably rinsed and dried. The protocol followed is then as follows:

1. wet the hands by passing them under running water, and shake them three times to drain the water,
2. place 1 g of product in the palm of one of the hands,
3. work the product between the two palms for 10 seconds, 4. add 2 ml of water and work the product again for 10 seconds,
5. rinse the hands under water,
6. dry them.

The criteria are evaluated at each step of the protocol followed, and they are graded on a scale from 0 to 10.

Step 3: evaluation of the covering power: the grade attributed is proportionately higher the less the skin can be seen through the product spread on.

Step 4: evaluation of the foam quality

The foam volume: the grade given is proportionately higher the greater the volume.

The size of the bubbles of which the foam is formed: the grade given is proportionately higher the larger the bubbles.

The density: foam consistency and behavior: the grade given is proportionately higher the greater the density.

The foam softness: the grade given is proportionately higher the softer the foam.

Step 5: evaluation during rinsing

The rinsing: the grade given is proportionately lower the greater the presence of a slippery film which is difficult to remove.

The sensory results for each of the criteria are given in the following table:

|  | Comparative Ex. 1 | Comparative Ex. 2 | Ex. 1 according to the invention | Ex. 2 according to the invention |
|---|---|---|---|---|
| Speed of appearance of first bubbles | 10 | 9.5 | 9.8 | 10 |
| Covering power | 6.3 | 4.6 | 6.4 | 6.4 |
| Foam volume | 6.4 | 6.8 | 6.4 | 6.1 |
| Size of the bubbles | 4.5 | 5 | 3.9 | 3.8 |
| Density | 6.9 | 6.8 | 7.4 | 7.1 |
| Foam softness | 6.4 | 6.1 | 6.9 | 5.8 |
| Rinsing | 6.9 | 7.3 | 7.3 | 8.4 |

The difference between the two different values should be greater than or equal to 1 in order to be significant.

As shown in the above table, the addition of hydrophobic silica and of oxyethylenated compound, while giving the thicker cleansing composition better rheological properties, does not change the performance qualities of the foam obtained, and, what is more, an improvement in certain criteria such as the size of the bubbles (and thus the fineness of the foam) and, in the case of Example 1 with sodium laureth sulfate (2.2 EO) and cocobetaine as surfactant system, an improvement in the foam softness are noted.

The disclosure of French priority Application Number 0009226 filed Jul. 13, 2000 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A cleansing composition, comprising:
(1) at least one foaming surfactant, (2) at least one hydrophobic silica and (3) at least one oxyalkylenated compound thickening agent in a physiologically acceptable aqueous medium comprising at least 35% by weight of water relative to the total weight of the composition, wherein the amount of hydrophobic silica ranges from 1% to 15% on an active material weight basis relative to the total weight of the composition.

2. The composition of claim 1, which comprises from 35% to 95% by weight of water relative to the total weight of the composition.

3. The composition of claim 1, which has a viscosity ranging from 7 to 20 Pa·s.

4. The composition of claim 1, wherein the hydrophobic silica is selected from the group consisting of amorphous silicas of pyrogenic origin.

5. The composition of claim 1, wherein the hydrophobic silica is selected from the group consisting of silicas having a specific surface ranging from 50 to 500 m$_2$/g, a number-average particle size ranging from 3 to 50 nm and a compacted density ranging from 40 to 200 g/l.

6. The composition of claim 1, wherein the amount of oxyalkylenated compound ranges from 1% to 20% on an active material weight basis relative to the total weight of the composition.

7. The composition of claim 1, wherein the oxyalkylenated compound is selected from the group consisting of polyethylene glycols, polyethylene glycol esters, polypropylene glycol esters, polyethylene glycol ethers, polypropylene glycol ethers, alkoxylated alkyl derivatives of polyols, oxyalkylenated triesters of glycerol, oxyalkylenated triesters of fatty acids, ethoxyethylenated urethane derivatives modified with alkyl chains, and mixtures thereof.

8. The composition of claim 7, wherein the polyethylene glycol esters have the formula:

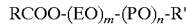

wherein $0 < m \leq 300$ and $0 \leq n\ 300$ and $m+n \geq 6$, R and R' represent, independently of each other, hydrogen or a saturated or unsaturated, linear or branched, hydroxylated or non-hydroxylated alkyl chain containing from 1 to 30 carbon atoms, or an aryl chain, with the proviso that R and R' are not simultaneously hydrogen.

9. The composition of claim 7, wherein the polyethylene glycol ethers and/or polypropylene glycol ethers have the formula:

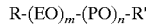

in which $0 \leq m \leq 300$ and $0 \leq n \leq 300$ and $m+n \geq 6$, R and R' represent, independently of each other, hydrogen or a saturated or unsaturated, linear or branched, hydroxylated or non-hydroxylated alkyl chain containing from 1 to 30 carbon atoms, or an aryl chain, with the proviso that R and R' are not simultaneously hydrogen.

10. The composition of claim 1, wherein the foaming surfactant is selected from the group consisting of nonionic surfactants, anionic surfactants, amphoteric surfactants and zwitterionic surfactants, and mixtures thereof.

11. The composition of claim 1, wherein the amount of foaming surfactant ranges from 2% to 50% on an active material weight basis relative to the total weight of the composition.

12. The composition of claim 1, wherein the foaming surfactant is selected from the group consisting of alkyl polyglucosides, maltose esters, polyglycerolated fatty alcohols, glucamine derivatives, carboxylates, amino acid derivatives, alkyl sulfates, alkyl ether sulfates, sulfonates, isethionates, taurates, sulfosuccinates, alkyl sulfoacetates, phosphates and alkyl phosphates, polypeptides, anionic alkyl polyglucoside derivatives, fatty acid soaps, betaines, N-alkylamidobetaines and derivatives thereof, glycine derivatives, sultaines, alkyl polyaminocarboxylates and alkylamphoacetates, and mixtures thereof.

13. The composition of claim 10, wherein the foaming surfactant is selected from the group consisting of an anionic surfactant which is an acylsarcosinate, an oxyethylenated alkyl ether sulfate, an N-aryl N-methyltaurate, an N-acylglutamate, an acylisethionate, an sulfosuccinate, a phosphate or an alkyl phosphate; a polypeptide or a soap; an amphoteric or zwitterionic surfactant which is a betaine or an alkylamphoacetate; a nonionic surfactant which is an alkyl polyglucoside, O-octanoyl-6'-D-maltose, O-dodecanoyl-6'-D-maltose, polyglycerolated dodecanediol (3.5 mole of glycerol) and 2-ethylhexyloxycarbonyl-N-methylglucamine; and mixtures of these surfactants.

14. The composition of claim 1, which further comprises at least one solvent selected from the group consisting of alcohols comprising from 1 to 6 carbon atoms and polyols, and mixtures thereof.

15. A method of treating the skin, the eyes, the scalp and/or the hair, comprising:
    applying the composition of claim 1 to the skin, the eyes, the scalp and/or the hair thereby cleansing and/or removing make-up from the skin, the eyes, the scalp and/or the hair.

16. A method of treating greasy skin, comprising:
    applying the composition of claim 1 to the skin, thereby removing grease from the skin.

17. A method of disinfecting the skin and/or the scalp, comprising:
    applying the composition of claim 1 to the skin and/or the scalp, thereby disinfecting the skin and/or the scalp.

18. A method of cleansing the skin, the eyes, the scalp and/or the hair, comprising:
    applying the composition of claim 1 to the skin, the eyes, the scalp and/or the hair in the presence of water thereby forming a lather; and
    removing the lather containing soiling residues by rinsing the lather from the skin, the eyes, the scalp and/or the hair with water.

19. A cosmetic mask, comprising:
    an applied composition of claim 1 as a mask on the skin of the face.

20. The composition of claim 1, wherein the amount of hydrophobic silica ranges from 2% to 10% on an active material weight basis relative to the total weight of the composition.

21. The composition of claim 20, wherein the amount of hydrophobic silica ranges from 2% to 6% on an active material weight basis relative to the total weight of the composition.

22. A cleansing composition, comprising:
    (1) at least one foaming surfactant, (2) at least one hydrophobic silica and (3) at least one oxyalkylenated compound in a physiologically acceptable aqueous medium comprising at least 35% by weight of water relative to the total weight of the composition, wherein the oxyalkylenated compound is a thickening agent selected from the group consisting of polyethylene glycols, polyethylene glycol esters, polypropylene glycol esters, polyethylene glycol ethers, polypropylene glycol ethers, alkoxylated alkyl derivatives of polyols, oxyalkylenated triesters of glycerol, oxyalkylenated triesters of fatty acids, ethoxyethylenated urethane derivatives modified with alkyl chains, and mixtures thereof.

23. The composition of claim 22, wherein the amount of silica(s) is at least 1% on an active material weight basis relative to the total weight of the composition.

24. The composition of claim 23, wherein the amount of hydrophobic silica ranges from 2% to 10% on an active material weight basis relative to the total weight of the composition.

25. The composition of claim 24, wherein the amount of hydrophobic silica ranges from 2% to 6% on an active material weight basis relative to the total weight of the composition.

26. The composition of claim 22, wherein the polyethylene glycol esters have the formula:

$$RCOO\text{-}(EO)_m\text{-}(PO)_n\text{-}R'$$

wherein $0 < m \leq 300$ and $0 \leq n \leq 300$ and $m+n \geq 6$, R and R' represent, independently of each other, hydrogen or a saturated or unsaturated, linear or branched, hydroxylated or non-hydroxylated alkyl chain containing from 1 to 30 carbon atoms, or an aryl chain, with the proviso that R and R' are not simultaneously hydrogen.

27. The composition of claim 22, wherein the polyethylene glycol ethers and/or polypropylene glycol ethers have the formula:

$$R\text{-}(EO)_m\text{-}(PO)_n\text{-}R'$$

in which $0 \leq m \leq 300$ and $0 \leq n \leq 300$ and $m+n \geq 6$, R and R' represent, independently of each other, hydrogen or a saturated or unsaturated, linear or branched, hydroxylated or non-hydroxylated alkyl chain containing from 1 to 30 carbon atoms, or an aryl chain, with the proviso that R and R' are not simultaneously hydrogen.

28. The composition of claim 1, which has a viscosity ranging from 9 to 15 Pa·s.

* * * * *

UNITED STATES PATENT AND TRADEMARK OFFICE
CERTIFICATE OF CORRECTION

PATENT NO. : 6,821,942 B2
DATED : November 23, 2004
INVENTOR(S) : Laurence Sebillotte-Arnaud et al.

It is certified that error appears in the above-identified patent and that said Letters Patent is hereby corrected as shown below:

Column 14,
Line 34, change "$\leq n300$" to -- $\leq n \leq 300$ --.

Column 16,
Line 32, change "$\leq n300$" to -- $\leq n \leq 300$ --.

Signed and Sealed this

First Day of March, 2005

JON W. DUDAS
*Director of the United States Patent and Trademark Office*